United States Patent [19]

Heimer et al.

[11] 4,056,673

[45] Nov. 1, 1977

[54] PHOSPHONOACETIC ACID DERIVATIVES OF NUCLEOSIDES

[75] Inventors: Edgar Philip Heimer, Cedar Grove; Alexander Leopold Nussbaum, Upper Montclair, both of N.J.

[73] Assignee: Hoffmann-La Roche Inc., Nutley, N.J.

[21] Appl. No.: 706,041

[22] Filed: July 16, 1976

[51] Int. Cl.$^2$ ............... C07H 19/10; C07H 19/20
[52] U.S. Cl. ................................ 536/27; 424/180; 536/28; 536/29
[58] Field of Search ............... 536/27, 28, 29, 26

[56] References Cited

U.S. PATENT DOCUMENTS

| | | |
|---|---|---|
| 3,201,389 | 8/1965 | Fujimoto et al. ............... 536/27 |
| 3,238,191 | 3/1966 | Myers ............................. 536/27 |
| 3,433,783 | 3/1969 | Honja et al. .................... 536/27 |
| 3,560,478 | 2/1971 | Myers ............................. 536/27 |

*Primary Examiner*—Johnnie R. Brown
*Attorney, Agent, or Firm*—Samuel L. Welt; Jon S. Saxe; George M. Gould

[57] ABSTRACT

Phosphonoacetic acid derivatives of purine and pyrimidine nucleosides are novel antiviral and/or antineoplastic agents.

13 Claims, No Drawings

PHOSPHONOACETIC ACID DERIVATIVES OF NUCLEOSIDES

BACKGROUND OF THE INVENTION

Phosphonoacetic acid has been known for over fifty years now. It was only recently, however, that it was discovered that this compound was an antiviral agent exhibiting oral and topical activity against herpes simlpex infection. See in this regard the paper by Shipkowitz et al., Applied Microbiology 26, No. 3, 264 (1973).

It has also been found that phosphonoacetic is useful in combating Marek's disease in poultry. U.S. Pat. No. 3,836,650, issued Oct. 4, 1974.

The antiviral activity of phosphonoacetic acid may be due to the inhibition of the virus'ability to replicate when the compound is administered. This inhibition is believed due to the inhibition of deoxyribonucleic acid synthesis in the virus. See Overby et. al., Antimicrobial Agents and Chemotherapy, 6, No. 3, 360 (1974).

DESCRIPTION OF THE INVENTION

The present invention relates to novel phosphonoacetic acid derivatives of purine and pyrimidine nucleosides which compounds have antiviral and/or antineoplastic activity. The compounds of the instant invention can be conveniently defined according to the following formula:

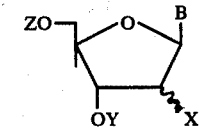

wherein B is selected from (a) the group of nucleobases consisting of adenine, guanine, cytidine, thymidine and uracil or (b) a 5-halopyrimidine; X is hydrogen, hydroxy or

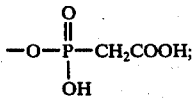

and Y is hydrogen or

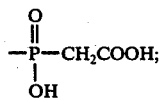

and Z is

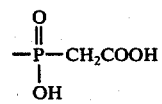

or, when either of X and Y is other than hydrogen or hydroxy, is hydrogen; and base salts thereof.

Examples of preferred compounds of formula I include adenosine-5'-mono-carboxymethylphosphonate, 2'-deoxyadenosine-5'-mono-carboxymethylphosphonate, guanosine-5'-mono-carboxymethylphosphonate, 5'-fluoro-2'-deoxyuridine-5'-mono-carboxymethylphosphonate, adenosine-2'(3')-5'-bis-carboxymethylphosphonate), 5-iodo-2'-deoxyuridine-5'-mono-carboxymethylphosphonate, arabinoadenosine-5'-mono-carboxymethylphosphonate and 5-bromo-2'-deoxyuridine-5'mono-carboxymethylphosphonate, thymidine-5'-mono-carboxymethylphosphonate and uridine-5'-mono-carboxymethylphosphonate.

The compounds of the present invention are conveniently prepared by treating the appropriately blocked nucleoside or 5-halopyrimidine with ethylphosphonoacetic acid (EPAA) activated with tri-isopropylbenzenesulfonyl chloride or alternate condensation agents in a manner known per se. This reaction is conveniently carried out at about room temperature. A polar solvent compound such as pyridine is employed as solvent for this reaction.

The resulting crude, blocked intermediate is then hydrolyzed preferably with dilute base such as 1 to 2N sodium hydroxide for base labile blocking groups or with an organic acid such as 95% formic acid for acid labile blocking groups. The desired product is isolated by utilizing conventional procedures such as, for example, by ion exchange chromatography followed by precipitation from an aqueous organic solvent such as acetone, or by lyophilization.

The phosphonoacetic acid derivatives of the present invention form base salts with pharmaceutically acceptable bases. Preferred base salts include the alkali metal salts such as sodium or potassium or the alkaline earth metal salts such as calcium.

The compounds of formula I and their salts are useful as antiviral agents, particularly against herpes simplex type 1 and type 2 virus and/or as antineoplastic agents. Compounds of formula I where B is 5-halopyrimidine are particularly active as antineoplastic agents.

The compounds of the instant invention and their salts are used in the form of conventional pharmaceutical preparations which contain said compounds in connection with conventional pharmaceutical organic or inorganic materials suitable for internal administration. The present compounds are administered parenterally with suitable antiviral dosages being in the range of from about 10 to 200 mg/kg and antineoplastic dosages being in the range of from about 0.1 to 50 mg/kg. These dosages can be administered in a single dosage form or in divided dosage forms.

The said pharmaceutical compositions can contain conventional parenteral organic or inorganic inert carrier materials such as water, vegetable oils, polyalkylene glycols and the like. These compositions can be submitted to conventional pharmaceutical expedients such as sterilization and/or can contain conventional pharmaceutical additives such as preservatives, stabilizing agents, wetting agents, emulsifying agents, salts for adjusting the osmotic pressure, buffers or the like. They can also contain other therapeutically useful materials.

The term halo as used herein is meant to include chloro, bromo, iodo or fluoro.

EXAMPLE 1

General Procedures

Ethyl phosphonoacetic acid (EPAA) was activated with triisopropylbenzenesulfonyl chloride (TPS) in dry pyridine and the appropriately blocked nucleoside was added. After two hours of stirring at room temperature the mixture was cooled and treated with cold water. After overnight storage at room temperature, the mixture was concentrated in vacuo and the blocking groups removed. Acid labile groups were hydrolyzed with 95% formic acid and base labile with 2N sodium hydroxide. The alkaline hydrolysis mixture was neutralized with Dowex 50 (hydrogen form) and filtered. During evaporation of the filtrate the mixture was frequently filtered to remove the formed triisopropylbenzenesulfonic acid. Column chromatography was carried out, unless otherwise indicated, with Dowex-1 (formate cycle) in an appropriate size column. The column was eluted with a formic acid gradient and fractions were collected. The fractions containing the desired product were pooled, concentrated, dissolved in water* and converted into the sodium salt by passage through a Dowex-50 column (sodium form). After concentration of the eluant the residue was either lyophilized or dissolved in a small volume of water and precipitated from a large excess of acetone. Analytical samples were dried at 60°/0.1 mmHg. Paper chromatography was performed by the ascending technique using acetonitrile: 0.1 M ammonium acetate pH 7 (60:40, v/v). Paper electrophoresis was employed using 0.05M triethylammonium bicarbonate (TEAB) pH 7.5 and Whatman 3MM paper at 26.5 V/cm for 1 hr. Phosphorous compounds were detected according to the methods of Hanes and Isherwood, Nature, 164, 1107 (1949).

*Occasionally samples were decolorized with carbopack B. (Supelco, Inc. Bellefonte. Penna.).

EXAMPLE 2

Adenosine-5'-mono-carboxymethylphosphonate

The above captioned compound was prepared using the general procedure of Example 1 and employing the following specific materials and quantities: Phosphorylation: EPAA, (96.6 g, 575 mmol); N-[(dimethylamino)methylene]-2',3'-O-isopropylidene-adenosine, (41.6 g, 115 mmol); TPS, (208 g, 690 mmol) pyridine; 1l. hydrolysis: 95% formic acid, overnight; 2N sodium hydroxide, 2.5 1.2 hr. Chromatography: Dowex-1 (formate), 2,25M formic acid. Yield: 40 g. (70%). Homogeneous on paper chromatography and electrophoresis. NMR (D$_2$O) δ 3.3 (d, 2, J = 21Hz,

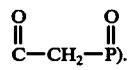

$\lambda_{max}^{H_2O}$ 258 mµ (ε 15,160). Anal. Calcd. for C$_{12}$H$_{14}$N$_5$O$_8$Na$_2$P = C, 33.27; H, 3,26; N, 16.17; P, 7.15. Found: C, 33.18; H, 3.22; N, 16.20; P, 7.20.

The starting material may be prepared as follows:

A suspension of 2',3'-O-isopropylidene-adenosine, (50 g., 163 mmol), anhydrous DMF (310 ml.) and N,N-dimethylformamide dimethyl acetal (65 ml.) was stirred at room temperature. After one hour, a homogeneous solution was obtained and left stirring overnight. The mixture was concentrated in vacuo (water bath temperature 40° C.) and the gum dissolved in chloroform (500 ml). Precipitation from petroleum ether (6.1) and drying over P$_2$O$_5$ at 0.1 mm Hg yielded 56.2 g. (95%) of the product N-[(dimethylamino)methylene]-2',3'-O-isopropylidene-adenosine. TLC (12.5% MeOH in chloroform) showed a single band (Rf. 0.56); m.p. 172°–173°; $\lambda_{max}^{H_2O}$ 228 (ε 12,200) and 309 (ε 31,400).

EXAMPLE 3

Uridine-5'-mono-carboxymethylphosphonate

The above-captioned compound was prepared using the general procedure of Example 1 and employing the following specific materials and quantities:

Phosphorylation: EPAA, (24.3 g., 145 mmol); 2',3'-O-isopropylidene uridine, (8.3 g., 29 mmol); TPS, (52 g., 174 mmol); pyridine 290 ml. Hydrolysis: 95% formic acid, overnight; 2N sodium hydroxide 300 ml., 2 hr. Chromatography: Dowex-1 (formate), 8M formic acid. Yield: 5.8 g. (48.5). Homogenous on paper chromatography and electrophoresis. NMR (D$_2$O) δ 3.24 (d, 2, J = 20.8 Hz,

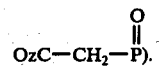

$\lambda_{max}^{H_2O}$ 261 (ε 9,640). Anal. Calcd. for C$_{11}$H$_{13}$N$_2$O$_{10}$NaP: C, 32.21; H, 3.19; N, 6,83; P, 7.55. Found: C, 32.07; H, 3,50; N, 6.96; P, 7.46.

EXAMPLE 4

5-Fluoro-2-deoxyuridine-5'-mono-carboxymethylphosphonate

The above captioned compound was prepared using the general procedure of Example 1 and employing the following specific materials and quantities:

Phosphorylation: EPAA, (58.8 g, 350 mmol); 3'-O-acetyl-5-fluoro-2'-deoxyuridine, (20.16 g, 70 mmol); TPS, (126.8 g, 420 mmol); pyridine, 700 ml. Hydrolysis: 2N sodium hydroxide. Chromatography: Sephadex G-10. Yield: 1.7 g. (45%) homogeneous on paper chromatography and electrophoresis. NMR (D$_2$O) δ 3.28 (d, 2, J = 20Hz;

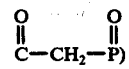

$\lambda_{max}^{H_2O}$ 268 (ε 8,100). Anal. Calcd: C$_{11}$H$_{12}$FNa$_2$O$_9$P 1.5 H$_2$O: C, 30.1; H,3.41; N, 6.37; P, 7.06. Found: C, 30.2; H, 3,97; N, 5.64; P, 6.40.

EXAMPLE 5

Guanosine-5'-mono-carboxymethylphosphonate

The above captioned compound was prepared using the general procedure of Example 1 and employing the following specific materials and quantities. Phosphorylation: EPAA, (11.2 g., 66 mmol); N$^2$O$^{2'}$O$^{3'}$-triacetyl-guanosine (5.4 g., 13.2 mmol); TPS, (23.8 g., 79.2 mmol); pyridine, (140 ml.). Hydrolysis: 2N sodium hydroxide, 400 ml. 2 hr. Column chromatography Sephadex G-10. Yield 2 g. (33%). Homogenous on paper chromatography NMR (D$_2$O) δ 3.2 (d, 2, J = 21 Hz,

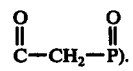

$\lambda_{max}^{H_2O}$ 275 sh (ε 8,600), 253-4 (ε 13,220). Anal. Calcd. for C$_{12}$H$_{14}$N$_5$O$_9$P: C, 32.08; H, 3.19; N, 15.58; P, 6.90. Found: C, 32.10; H, 3.39; N, 15.66; P, 6.65.

EXAMPLE 6

Fluorouridine-5'-mono-carboxymethylphosphonate

The above captioned compound was prepared using the general procedure of Example 1 and employing the following specific materials and quantities:

Phosphorylation: EPAA, (6.72 g, 40 mmol); 2',3'-O-isopropylidene-5-fluorouridine, (2.4 g, 8 mmol); TPS (14.5 g, 48 mmol); pyridine, (80 ml.). Hydrolysis: 95% Formic acid, overnight; 2N sodium hydroxide, 240 ml., 2 hr. Column chromatography: Dowex-1 (formate), 6M formic acid. Yield: 2.84 g. (55%). Homogeneous on paper chromatography. NMR (D₂O) δ 3.45 (d, 2, j = 21 Hz,

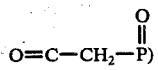

$\lambda_{max}^{H_2O}$ 269 (ε 8,500). Anal. Calcd. for $C_{11}H_{12}FN_2Na_2$-$O_{10}P \cdot 0.4H_2O$: C, 29.93; H, 3.17; N, 6.23; P, 6.90. Found: C, 29.98; H, 3.38; N, 5.96; P, 6.80; H₂O (KF) 4.60%.

EXAMPLE 7

Thymidine-5'-mono-carboxymethylphosphonate

The above captioned compound was prepared using the general procedure of Example 1 and employing the following specific materials and quantities: Phosphorylation: EPAA, (17.6 g., 105 mmol); 3'-O-acetyl thymidine, (6 g, 21 mmol); TPS, (38 g, 126 mmol); Pyridine, (210 ml.). Hydrolysis: 2N sodium hydroxide, 300 ml. 2 hr. column chromatography: Dowex-1 (formate), 6.25 M formic acid. Yield 6.4 g. (75%). Homogenous on paper chromatography and electrophoresis. NMR (D₂O) δ 3.4 (d, 2, J = 21 Hz,

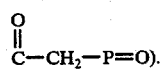

$\lambda_{max}^{H_2O}$ 266-7 (ε 9,600). Anal. Calcd. for $C_{12}H_{15}N_2Na_2$-$O_9P$: C, 35.31; H, 3.70; N, 6.86; P, 7.59. Found: C, 35.48; H, 3.93; N, 6.80; P, 8.0.

EXAMPLE 8

5-Iodo-2'-deoxyuridine-5'-mono-carboxymethylphosphonate

The above captioned compound was prepared using the general procedure of Example 1 and employing the following specific materials and quantities; Phosphorylation: EPAA, (7.2 g., 43 mmol); 3'-O-acetyl-5-iododeoxyuridine (3.4 g, 8.6 mmol); TPS, (15.5 g, 51.6 mmol); Pyridine, (80 ml.). Hydrolysis: 2N sodium hydroxide, 360 ml, 2 hr. Chromatography: Dowex-1 (formate) 11.3 N formic acid. Yield: 1.8 g. (45%). Homogenous on paper chromatography and electrophoresis. NMR (D₂O) δ 3.3 (d, 2, J = 21 Hz, O=C—CH₂—P=O). $\lambda_{max}^{H_2O}$ 286 (ε 6,800). Anal. Calcd. for $C_{11}H_{12}IN_2$-$Na_2O_9P \cdot H_2O$: C, 24.55; H, 2.62; N, 5.21; I, 23.58; P, 5.76. Found: C, 24.61; H, 3.10; N, 5.76; I, 23.76; P, 5.45. H₂O (KF), 4.60%.

EXAMPLE 9

Adenosine-2'-(or 3'),5'-bis-carboxymethylphosphonate

The above captioned compound was prepared using the general procedure of Example 1 and employing the following specific materials and quantities:
Phosphorylation: EPAA, (39.8 g., 237 mmol); N-benzoyladenosine (8.8 g., 23.7 mmol); TPS, (78.8 g, 261 mmol); pyridine, 475 ml. Hydrolysis: 2N sodium hydroxide 540 ml. 2 hours. conc. ammonium hydroxide, 900 ml., overnight. Column chromatography: DEAE-23, 0.32 M TEAB. Yield: 3.5 g. (35%). Homogeneous on paper electrophoresis. NMR (D₂O) δ 3.34 (d, 4, J = 20 Hz, O=C—CH₂—P=O). $\lambda_{max}^{H_2O}$ 259 (ε 14,000). Anal. Calcd. for $C_{14}H_{16}N_5O_{12}P_2Na_4 \cdot 0.5 (CH_3)_2C=O$. C, 29.60; H, 3.04; N, 11.13; P, 9.84. Found: C, 29.39; H, 3.30; N, 11.67; P, 9.70. NMR showed 0.5 M (CH₃)₂CO.

EXAMPLE 10

Arabinosyladenine-5'-mono-carboxymethylphosphonate

The above captioned compound was prepared using the general procedure of Example 1 and employing the following specific materials and quantities:

A. Via Blocked Nucleoside

Phosphorylation: EPAA (2.85 g., 17.0 mmol); N-benzoyl-9-[2,3-di-O-benzoyl-β-D-arabinofuranosyl]-adenine (1.6 gm., 3.4 mmol); TPS (6.2 g., 20.4 mmol); pyridine (34 ml.). Hydrolysis: 2N NaOH, 172 ml.; concentrated NH₄OH, 250 ml. Chromatography: Carbopack B. Yield: 0.41 g. (28%). Homogeneous on paper chromatography and paper electrophoresis. NMR (D₂O) δ 3.25

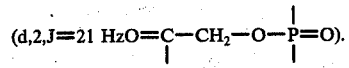

$\lambda_{max}^{H_2O}$ 259 (ε 13,000). Anal. Calcd. for $C_{12}H_{14}N_5Na_2$-$O_8P \cdot 1.55 H_2O$: P, 6.71. Found: P, 6.06; H₂O (K.F.), 6.45%.

B. Via Partially Protected Nucleoside

Phosphorylation: EPAA (3.24 g., 19.2 mmol); N-[(dimethylamino)methylene]arabinosyladenine (5.6 g., 17.4 mmol); TPS (8.65 g., 28.6 mmol); pyridine (170 ml.). Hydrolysis: 2N NaOH, 140 ml. Chromatography: Carbopack B. Yield: 4.44 g. (44.7%). Homogeneous on paper chromatography and paper electrophoresis. NMR (D₂O) δ 3.29 (d,2,J = 21 Hz O=C—CH₂—O—P=O). $\lambda_{max}^{H_2O}$ 259 (ε14,800). Anal. Calcd. for $C_{12}H_{14}N_5O_8PNa_2 \cdot 0.8 M H_2O$: C, 32.18; H, 3.48; N, 15.64; P, 6.91. Found: C, 31.76; H, 3.75; N, 15.20; P, 6.77. H₂O (K.F.) 3.37%.

EXAMPLE 11

5-Bromo-2'-deoxyuridine-5'-monocarboxymethylphosphonate

The above captioned compound was prepared using the general procedure of Example 1 and employing the following specific materials and quantities:
Phosphorylation: EPAA (7.39 g., 44 mmol); 3'-O-acetyl-5-bromodeoxyuridine (3.1 g., 8.8 mmol);TPS (15.9 g., 52.8 mmol); pyridine (88 ml.). Hydrolysis: 2N NaOH, 350 ml., 2 hours. Chromatography: Carbopack B. Yield: 2.64 (61%). Homogeneous on paper chromatography and paper electrophoresis. NMR (D₂O) δ 3.2

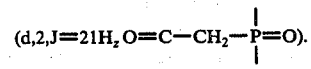

$\lambda_{max}^{H_2O}$ 279 (ε9,000). Anal. Calcd. for $C_{11}H_{12}BrNa_2O_9P \cdot 1.3 H_2O$: C, 26.60; H, 2.96; N, 5.63; P, 6.23. Found: C, 26.80; H, 3.12; N, 5.87; P, 6.18; H₂O (K.F.), 4.75%.

EXAMPLE 12

2'-Deoxyadenosine-5'-mono-carboxymethylphosphonate

The above captioned compound was prepared using the general procedure of Example 1 and employing the following specific materials and quantities:

A. Via Blocked Nucleoside

Phosphorylation: EPAA (2.04 g., 12.1 mmol); 3'-O-benzoyl-N-benzoyldeoxyadenosine (1.12 g., 2.43 mmol); TPS (4.4 g., 14.58 mmol); pyridine (20 ml.). Hydrolysis: 2N N$_9$OH, 80 ml., overnight. Chromatography: Supelco Carbopack B. Homogeneous on paper electrophoresis. NMR (D$_2$O) δ 3.26 (d,2,J = 21 Hz, O=C—CH$_2$—P=O). Anal. Calcd. for C$_{12}$H$_{14}$N$_5$Na$_2$O$_7$P . 1M (CH$_3$)$_2$CO: C, 34.91; H, 3.47; N, 16.55; P, 7.23. Found: C, 34.76; H, 3.70; N, 16.0; P, 6.93. 1 mole (CH$_3$)$_2$CO found by NMR, B. Via Partially Protected Nucleoside Phosphorylation: EPAA (3.5 g., 20 mmol); 2'-deoxy-N-[(dimethylamino) methylene]-adenosine (6.2 g., 20 mmol); TPS (6.65 g., 22 mmol); pyridine (200 ml.). Hydrolysis: 2N NaOH, 200 ml., 2 hours. Chromatography: Carbopack B. Yield: 3.1 g. (36%). Homogeneous on paper chromatography and paper electrophoresis. NMR (D$_2$O) δ 3.2 (d,2,J = 20.5 Hz, O=C—CH$_2$—P=O). $\lambda_{max}^{H_2O}$ 259 (ε 14,000). Anal. Calcd. for C$_{12}$H$_{14}$N$_5$Na$_2$O$_7$P . 1.55 M H$_2$O: C, 32.37; H, 3.84; N, 15.7; P, 6.95. Found: C, 32.88; H, 3.71; N, 15.63; P, 6.57. H$_2$O (K.F.) 6.70%.

EXAMPLE 13

Purine and pyrimidine derivatives of phosphonoacetic acid, disodium salt, were tested for activity against herpes simplex types 1 and 2, and pseudorabies virus infections in mice by the following procedure. Swiss albino mice weighing 9 to 12 grams received 0.5 ml. intraperitoneally of the test substances 24 hours before virus infection, immediately after virus infection (0 hr.) and again at 24 hours after virus infection for a total of three treatments. Control mice received 0.5 ml. of water intraperitoneally at the same time intervals (−24, 0, +24 hr). Twenty-four hours after the first treatment, drug-treated and water-treated mice were infected intraperitoneally with approximately 10 times the Lethal Dose$_{50}$(LD$_{50}$) of herpes simplex (types 1 and 2) virus or pseudorabies virus pools grown in primary rabbit kidney cell cultures. Mice were observed for 21 days after virus infection and the number of animals alive on day 21 was used to calculate the Protective Dose$_{50}$(PD$_{50}$) as described by Reed and Muench [Am. Jour, Hygiene 27: 493 (1938)].

The PD$_{50}$ values of purine and pyrimidine derivatives of phosphonacetic acid against herpes simplex type 1 virus infection in mice are as follows:

| | |
|---|---|
| Adenosine-5'-mono-carboxymethyl phosphonate | 180 mg/kg intraperitoneally |
| Adenosine-2'(or 3'), 5'-bis-carboxy-methylphosphonate | 197 mg/kg intraperitoneally |
| Guanosine-5'-mono-carboxymethyl-phosphonate | 144 mg/kg intraperitoneally |
| Thymidine-5'-mono-carboxymethyl-phosphonate | 185 mg/kg intraperitoneally |
| Uridine-5'-mono-carboxymethyl-phosphonate | 127 mg/kg intraperitoneally |
| 5-Iodo-2'-deoxyuridine-5'-mono-carboxy-methylphosphonate | 110 mg/kg intraperitoneally |
| 2'-Deoxyadenosine-5'-monocarboxy-methylphosphonate, monoacetonate | 444 mg/kg intraperitoneally |

The PD$_{50}$ of adenosine-5'-mono-carboxymethylphosphonate was 575 mg/kg intraperitoneally against herpes simplex type 2 virus infection in mice and 386 mg/kg intraperitoneally against pseudorabies virus infection in mice.

In Vitro Testing

Purine and pyrimidine derivatives of phosphonoacetic acid, disodium salt, were tested for in vitro antiviral activity against herpes simplex type 1 virus by the tube dilution assay. Monolayers of WI-38 human lung fibroblast cells were infected with serial ten-fold dilutions of herpes simplex type 1 virus. The mean tissue culture infective doses (TCID$_{50}$) of the virus-infected cultures in the presence and absence of non-cytotoxic doses of the test substances were determined on the basis of cytopathogenic effect after 7 days incubation at 37° C. The doses of test substances which inhibited the growth of herpes simplex type 1 virus by at least 2 logarithms (equivalent to 99% reduction in virus titer) are as follows:

| | |
|---|---|
| Adenosine-5'-mono-carboxymethyl-phosphonate | 250 μg/ml |
| Adenosine, (2' or 3'),5'-biscarboxy-methylphosphonate | >1000 μg/ml |
| Guanosine-5'-mono-carboxymethyl-phosphonate | <500 μg/ml |
| Thymidine-5'-mono-carboxymethyl-phosphonate | 500 μg/ml |
| Uridine-5'-mono-carboxymethyl-phosphonate | 125 μg/ml |
| 5-Iodo-2'-deoxyuridine-5'-mono-carboxymethylphosphonate | <25 g/ml |
| 2'-Deoxyadenosine-5'-mono-carboxy-methylphosphonate | <500 g/ml |
| Arabinoadenosine-5'-mono-carboxymethyl phosphonate | <500 g/ml |
| 5-Bromo-2'-deoxyuridine-5'-mono-carboxy-methylphosphonate | <1000 g/ml. |

EXAMPLE 14

The effects of 5-fluorodeoxyuridine-5'-monocarboxymethylphosphonate (Compound A) and 5-fluoro-2'-deoxyuridine (FUDR) were tested against experimental tumors in mice (sarcoma 180, Ehrlich carcinoma, KA-31, and leukemia L1210 ascites) by the following procedures. Sarcoma 180 and Ehrlich carcinoma solid tumors were induced in Swiss albino mice weighing 18–20 grams by either subcutaneous (ventrolateral) implantation of 20–100 mg of tumor material (sarcoma 180) or by subcutaneous injection of 0.5 ml. of 1–10 saline-diluted ascitic tumor cell suspensions (Ehrlich carcinoma). KA-31 solid tumors were produced in BALB/c mice, 18–20 g, by the subcutaneous implantation of 2 × 10$^5$ non-producer murine sarcoma virus-transformed BALB/3T3 cells.

Mice implanted with sarcoma 180 to Ehrlich carcinoma solid tumors received 1.0 ml. intraperitoneally of the test substances or water shortly after implantation and once daily thereafter for a total of 8 treatments. Mice bearing KA-31 solid tumor received 14 daily treatments. Mice were sacrificed 24 hours after the last treatment, tumors excised and the average weight of tumors in the drug-treated (T) group compared to the average weight of tumors in the water-treated group (C). A C/T index of $\geq 2$ indicated $\geq 50\%$ inhibition of tumor growth and antitumor effect.

Leukemia L1210 ascites was produced in 18-20 g. $BDF_1$ mice by the intraperitoneal implantation of $1 \times 10^6$ leukemic cells. Treatment, 1.0 ml. intraperitoneally, with the test substances (T) or water (C) was initiated 24 hours after implantation and continued daily thereafter for a total of 5 treatments. Animals were observed for 30 daus following implantation and the mean survival time of the drug-treated mice (T) compared with the mean survival time of the water-treated mice. A T/C index of $\geq 1.5$ indicated $\geq 50\%$ prolongation of mean survival time and an antitumor effect.

The effects of Compound A and FUDR against solid tumors in mice are shown in Table 1.

Table 1

Effects of Compound A and FUDR Against Solid Tumors in Mice

| Tumor | Drug | Dose mg/kg ip × 8 | No. survivors/ No. tested | C/T Index[1] | Activity |
|---|---|---|---|---|---|
| Sarcoma 180 | Cmpd. A | 50 | 16/16 | 5.9 | + |
|  |  | 25 | 8/8 | 2.2 | + |
|  |  | 12.5 | 8/8 | 1.7 | − |
|  | FUDR | 50 | 11/16 | 5.1 | + |
|  |  | 25 | 15/16 | 7.9 | + |
|  |  | 12.5 | 8/8 | 2.3 | + |
| Ehrlich carcinoma | Cmpd. A | 50 | 21/24 | 12.1 | + |
|  |  | 25 | 23/24 | 3.4 | + |
|  |  | 12.5 | 24/24 | 2.4 | + |
|  |  | 6.25 | 16/16 | 1.5 | − |
|  | FUDR | 50 | 30/32 | 12.4 | + |
|  |  | 25 | 29/31 | 4.4 | + |
|  |  | 12.5 | 16/16 | 3.3 | + |
|  |  | 6.25 | 8/8 | 1.0 | − |
| KA-31[2] | Cmpd. A | 25 | 15/24 | 13.8 | + |
|  |  | 12.5 | 19/24 | 3.8 | + |
|  |  | 6.25 | 21/23 | 1.8 | − |
|  | FUDR | 25 | 14/32 | 8.5 | + |
|  |  | 12.5 | 36/40 | 4.2 | + |
|  |  | 6.25 | 24/32 | 2.1 | + |
|  |  | 3.12 | 16/16 | 1.5 | − |

[1]C/T value of 2.0 or more (average weight of tumors in control animals divided by average weight of tumors in treated animals) indicated 50% inhibition and antitumor effect.
[2]Treatment administered ip × 14.

When tested against sarcoma 180, Compound A was active at doses of 50 and 25 mg/kg but inactive at 12.5 mg/kg. FUDR was active against sarcoma 180 at 50, 25 and 12.5 mg/kg. Compound A and FUDR were active against Ehrlich carcinoma at 50, 25, 12.5 mg/kg but inactive at 6.25 mg/kg. In the case of the KA-31 tumor, 14 ip treatments were administered and activity was observed with Compound A at 25 12.5 mg/kg but not at 6.25 mg/kg. FUDR was active against KA-31 solid tumor at doses of 25, 12.5 and 6.25 mg/kg but inactive at 3.12 mg/kg.

Compound A and FUDR were both inactive against leukemia L1210 ascites in $BDF_1$ mice when tested at 100 mg/kg intraperitoneally.

EXAMPLE 15

Parenteral Solution

A total of 500 mg. of adenosine-5'-mono-carboxymethyl phosphonate in lyophilized form or as a dry filled sterile solid was reconstituted with water or saline to a total volume of 10 ml. This provides a solution suitable for i.v. injection. For preparation of an i.v. infusion solution the aforesaid sterile solution is added to from 500 ml. to 1000 ml. of a 5% dextrose solution or 0.9% NaCl solution.

EXAMPLE 16

Parenteral Solution

A total of 125 mg. of 5-fluoro-deoxyuridine-5'-mono-carboxymethyl phosphonate in lyophilized form or as a dry filled sterile solid is reconstituted with water or saline to a total volume of 10 ml. This solution is suitable for i.v. infusion. To prepare an i.v. infusion solution, the aforesaid solution is added to from 500 ml. to 1000 ml. of 5% dextrose solution or 0.9% NaCl solution.

We claim:

1. A compound of the formula

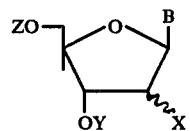

wherein B is selected from (a) the group of nucleobases consisting of adenine, guanine, cytidine, thymidine and uracil or (b) a 5-halopyrimidine; X is hydrogen, hydroxy, or

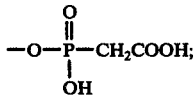

Y is hydrogen or

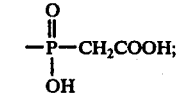

and Z is

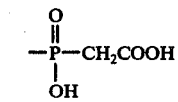

or, when either of X and Y is other than hydrogen or hydroxy, is hydrogen: and pharmaceutically acceptable base salts thereof.

2. The compound of claim 1 wherein B is a nucleobase consisting of adenine, guanine, cytidine, thymidine and uracil.

3. The compound of claim 2 which is adenosine-5'-mono-carboxymethylphosphonate.

4. The compound of claim 2 which is 2'-deoxyadenosine-5'-mono-carboxymethylphosphonate.

5. The compound of claim 2 which is guanosine-5'-mono-carboxymethylphosphonate.

6. The compound of claim 2 which is adenosine-2'(3')-5'-bis-(carboxymethylphosphonate).

7. The compound of claim 2 which is arabinoadenosine-5'-mono-carboxymethylphosphonate.

8. The compound of claim 2 which is thymidine-5'-mono-carboxymethylphosphonate.

9. The compound of claim 2 which is uridine-5'-mono-carboxymethylphosphonate.

10. The compound of claim 1 wherein B is a 5'-halopyrimidine.

11. The compound of claim 10 which is 5-fluoro-2'-deoxyuridine-5'-mono-carboxymethylphosphonate.

12. The compound of claim 10 which is 5-ioso-2'-deoxyuridine-5'-mono-carboxymethylphosphonate.

13. The compound of claim 10 which is 5-bromo-2'-deoxyuridine-5'-mono-carboxymethylphosphonate.

* * * * *